(12) United States Patent
Menart et al.

(10) Patent No.: US 7,906,109 B2
(45) Date of Patent: *Mar. 15, 2011

(54) PHARMACEUTICAL COMPOSITION COMPRISING AN ACTIVE PRINCIPAL AND SULPHOBETAINE

(75) Inventors: Viktor Menart, Logatec (SI); Vladka Gaberc Porekar, Ljubljana (SI); Barbara Podobnik, Ljubljana (SI)

(73) Assignee: Lek Pharmaceuticals d.d., Ljubljana (SL)

( * ) Notice: Subject to any disclaimer, the term of this patent is extended or adjusted under 35 U.S.C. 154(b) by 197 days.

This patent is subject to a terminal disclaimer.

(21) Appl. No.: 10/583,157

(22) PCT Filed: Dec. 22, 2004

(86) PCT No.: PCT/SI2004/000043
§ 371 (c)(1),
(2), (4) Date: Jun. 16, 2006

(87) PCT Pub. No.: WO2005/060989
PCT Pub. Date: Jul. 7, 2005

(65) Prior Publication Data
US 2007/0184019 A1 Aug. 9, 2007

(30) Foreign Application Priority Data
Dec. 23, 2003 (SI) .................................. 200300318

(51) Int. Cl.
*A61K 38/19* (2006.01)
*A61K 38/20* (2006.01)
*A61K 38/21* (2006.01)
*A61K 38/42* (2006.01)
*A61K 38/22* (2006.01)
*A61K 38/18* (2006.01)
*A61K 38/17* (2006.01)
*A61K 38/28* (2006.01)
*A61K 31/205* (2006.01)

(52) U.S. Cl. ..... 424/85.1; 514/554; 424/94.4; 424/85.2; 424/85.4

(58) Field of Classification Search .................. None
See application file for complete search history.

(56) References Cited

U.S. PATENT DOCUMENTS

| | | | |
|---|---|---|---|
| 5,500,416 A * | 3/1996 | Miyazawa et al. | 514/23 |
| 5,919,443 A | 7/1999 | Michaelis et al. | |
| 6,103,683 A | 8/2000 | Romano et al. | |
| 6,838,089 B1 | 1/2005 | Carlsson et al. | |

FOREIGN PATENT DOCUMENTS

WO   WO 2004015124 A1 *   2/2004

OTHER PUBLICATIONS

Vuillard et al., Biochem J. 1995;305:337-343.*
Vuillard et al., Interactions of non-detergent sulfobetaines with early folding intermediates facilitate in vitro protein renaturation (1998).

* cited by examiner

*Primary Examiner* — Cherie M Woodward
(74) *Attorney, Agent, or Firm* — Luedeka, Neely & Graham, P.C.

(57) ABSTRACT

The present invention relates to the pharmaceutical composition comprising a non-detergent sulphobetaine (NDSB).

11 Claims, 2 Drawing Sheets

PHARMACEUTICAL COMPOSITION COMPRISING AN ACTIVE PRINCIPAL AND SULPHOBETAINE

This application is a 371 National Phase of PCT Application Number PCT/SI2004/000043 entitled "A Pharmaceutical Composition Comprising an Active Principle Sulphobetaine" to Viktor Menart et al., filed on Dec. 22, 2004, and designating, among other countries/regions, the U.S., and which claims priority to Slovenian National Patent Application Number P-200300318 to Viktor Menart et al., filed on Dec. 23, 2003, the contents of which are incorporated herein by reference in their respective entireties.

FIELD OF THE ART

The present invention relates to a pharmaceutical composition which comprises a non-detergent sulphobetaine (NDSB).

STATE OF THE ART

Pharmaceutical compositions comprising active pharmaceutical ingredients are well known. The common pharmaceutical compositions described comprise various pharmaceutically acceptable excipients which with their different properties (e.g. stabilisation of the active pharmaceutical ingredient, adjustment and/or maintenance of the pH, effect on the solubility of the active pharmaceutical ingredient, maintenance of isotonicity of the pharmaceutical composition, etc.), enable usage of active pharmaceutical ingredients in the pharmaceutical compositions. Pharmaceutically acceptable excipients are extensively described; see e.g. Handbook of Pharmaceutical Excipients, Ainley Wade and Paul J. Weller, American Pharmaceutical Association, 1994.

Therapeutically active proteins have also been described as active pharmaceutical ingredients in the pharmaceutical compositions. These pharmaceutical compositions also comprise various pharmaceutical excipients which—with their properties—enable preparation of stable pharmaceutical compositions comprising therapeutically active proteins. Such pharmaceutical compositions are extensively described; see e.g. Yu-Chang John Wang and Musetta A. Hanson (1988), J of Parenteral Science & Technology, 42: S4-S26; Wong D. and Parasrampuria J. (1997), Biopharm: November 52-61.

Stable pharmaceutical compositions comprising therapeutic protein granulocyte-colony stimulating factor (G-CSF) are disclosed in EP 373679 and described so as to stabilise primarily the G-CSF in solution with low conductivity and acid pH between 2.75 and 4.0. To improve stability, various sugars, amino acids, polymers and detergents were added. It has been particularly emphasized that pH of the G-CSF comprising composition should be less than 4 in order to reduce formation of aggregates and increase stability in this way. The formation of aggregates and reduced stability with a pH exceeding 4.0 are in accordance with the data from literature from the state of art (Kuzniar et al. (2001), *Pharm Dev Technol* 6(3): 441-7; Bartkowski et al. (2002), *J Protein Chem* 21(3):137-43; Narhi et al. (1991), *J Protein Chem* 10(4): 359-367; Wang W (1999), *Int J Pharmaceut* 185:129-188. G-CSF stability, described in other pharmaceutical compositions from patent and scientific literature, was achieved with addition of various stabilisers, such as e.g. sulphate ions (EP 1129720), mixture of various preservatives, amino acids and surfactants (EP 607156), various buffer systems (phosphate, citrate, arginine, acetate) in the presence of a surfactant (EP 674525), high molecular compounds, such as hydroxypropyl cellulose, polyethylene glycol, polyvinyl alcohol, polyvinylpirrolidone and others (GB 2193621), a surfactant (EP 1060746), various buffer systems (TRIS, HEPES, TRICINE) (EP 0988861), sugars, such as cellobiose, gentiobiose, isomaltose, raffinose, trehalose and others (EP 0674524), and one or more amino acids (EP 1197221, WO51629, EP 1260230 and EP 1329224, EP 0975335). Although low ionic strength is preferred in the G-CSF comprising pharmaceutical compositions, various surfactants and other stabilisers are used for G-CSF stabilisation in the majority of cases have been described to be used for G-CSF stabilisation. Moreover, various buffer systems have been used additionally in the majority of cases for the maintenance of pH.

In the literature the use of non-detergent sulfobetaines (NDSBs) as solubilisers was described (used in high concentrations of around 1 M of the solution) by protein renaturations (Chong Y and Chen H. (2000), Biotechiques 29(6): 1166-7; Vuillard L et al. (1995), Biochem J 305: 337-43; Vuillard L et al. (1995), Electrophoresis 16(3): 295-7; Vuillard L et al. (1998), Eur J Biochem 256: 128-135; Goldberg M E et al. (1995), Folding & Design 1: 21-27).

There is an ongoing need to provide stabilised pharmaceutical compositions. A description of NDSBs in pharmaceutical compositions has not been found either in the scientific or in the patent literature.

DESCRIPTION OF THE INVENTION

Figure 1:
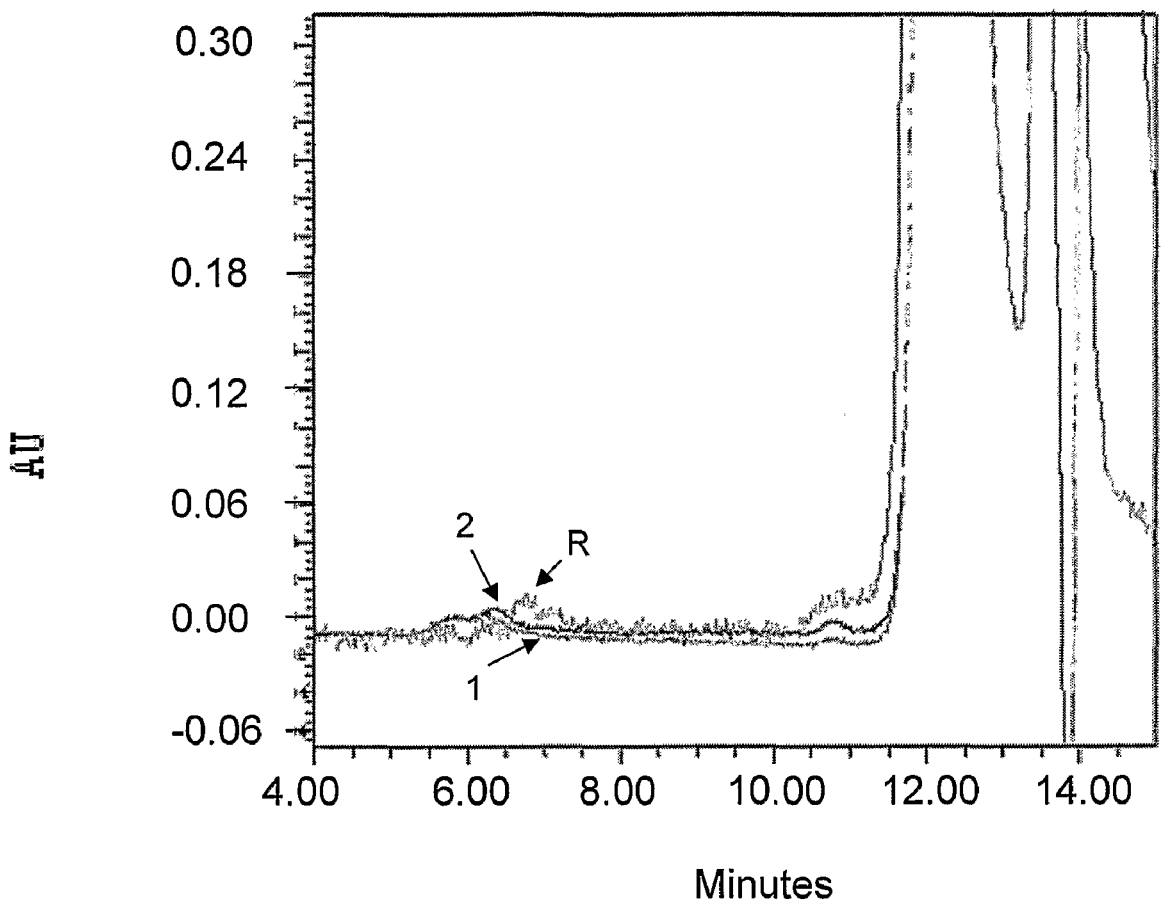
FIG. 1: SE-HPLC of invention samples and of reference sample, stored at 40° C. (±2° C.) for 1 month (40).

In the context of the present invention it has been discovered that a NDSB can be used as an excipient in a pharmaceutical composition. By using a NDSB pharmaceutical compositions can be provided which are stabilised.

Accordingly, the present invention relates to a pharmaceutical composition comprising a NDSB.

In a first aspect of the present invention a pharmaceutical composition is provided which comprises an active pharmaceutical ingredient and a non-detergent sulfobetaine (NDSB).

The active pharmaceutical ingredient of the present invention is selected from the group consisting of a therapeutically effective synthetic or natural organic molecule (e.g. poorly water-soluble synthetic and natural organic molecules), and a therapeutically effective protein (e.g. poorly water-soluble and/or hydrophobic proteins) and/or other active pharmaceutical ingredients having a therapeutic effect. The active pharmaceutical ingredient is preferably comprised in a therapeutically effective amount. The term >>therapeutically effective amount of active pharmaceutical ingredient<< as used herein, refers to active pharmaceutical ingredient in the amount having a therapeutic effect The pharmaceutical composition of the present invention comprises a non-detergent sulphobetaine (NDSB).

The term >>non-detergent sulphobetaine<< as used herein, refers to a sulphobetaine which does not form micelles in water solution.

In a preferred embodiment of the pharmaceutical composition of the present invention, the NDSB is quaternary ammonium salt where the groups R1, R2, R3 and R4-SO$^-_3$ are bound to the central nitrogen atom, and where:

R1 is methyl, ethyl, propyl, butyl, pentyl, hexyl or their derivatives;

R2 is methyl, ethyl, propyl, butyl, pentyl, hexyl or their derivatives;

R3 is methyl, ethyl, propyl, butyl, pentyl, hexyl or their derivatives, and all combinations of R1, R2 and R3, and R4 is $(CH_2)_n$, wherein n is between 1 and 6; most preferred n is 3.

Quaternary nitrogen atom can be a part of aliphatic or aromatic ring structure as well.

Accordingly, in a preferred embodiment of the pharmaceutical composition of the present invention, the NDSB is quaternary ammonium salt of Formula 1,

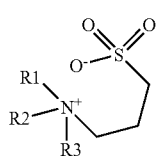

Formula 1 wherein R1, R2 and R3 can be the same and/or different and are selected from the group consisting of methyl, ethyl, propyl, butyl, pentyl, hexyl or their derivatives, and R4 is $(CH_2)_n$, wherein n is between 1 and 6; most preferably n is 3.

Preferably, in the pharmaceutical composition of the present invention the NDSB which is selected from the group consisting of dimethylethyl-(3-sulphopropyl)-ammonium salt (SB195, Vuillard et al (1 994) FEBS Letters, 353, 294-296; Goldberg et al (1995/1996) Folding & Design, 1, 21-27), 3-(1-pyridino)-1-propanesulfonate (SB201), dimethylbenzylammonium propanesulfonate (SB256), dimethyl-t-butyl-(3-sulphopropyl) ammonium salt (SB222t), 3-(1-methylpiperidine)-1-propanesulfonate (SB221) and dimethyl-(2-hydroxyethyl)-(sulphopropyl)-ammonium salt (SB211; Vuillard et al (1995) Anal Biochem, 230, 290-294) is used. Two ore more of indicated NDSBs can be also used in all possible combinations. Preferably dimethyl-t-butyl-(3-sulphopropyl) ammonium salt (SB222t), dimethylethyl-(3-sulphopropyl)-ammonium salt (SB195) and 3-(1-methylpiperidine)-1-propanesulfonate (SB221) are used. Most preferably dimethyl-t-butyl-(3-sulphopropyl) ammonium salt (SB222t) is used.

The concentration of NDSB used depends on the pH intended to be adjusted and/or maintained. It is selected from the range from 1 to 1000 mM, preferably from 5 to 100 mM. pH of the pharmaceutical composition of the present invention may be within the range from 2 to 9, preferably between 3 and 8, and most preferably from 3.5 to 7.5.

In a second aspect of the present invention the pharmaceutical composition is provided which comprises a therapeutically effective protein and a non-detergent sulfobetaine (NDSB).

The term >>therapeutically effective protein<<0 as used herein, refers to a protein with therapeutic effect. A therapeutically effective protein used in the pharmaceutical composition of the present invention is selected from the group consisting of granulocyte colony-stimulating factor (G-CSF), interferons (IFNs); such as IFN-alpha2a, INF-alpha 2b, IFN-beta, IFN-gamma 1b; interleukins(ILs), such as IL-1, IL-2, IL-3, IL-4, IL-5 to IL-10; granulocyte-macrophage colony-stimulating factor (GM-CSF); macrophage colony-stimulating factor (M-CSF); epidermal growth factor (EGF); erythropoietin (EPO); follicle-stimulating hormone (FSH); human serum albumin (HSA); deoxyribonuclease (DNAse); fibroblast growth factor (aFGF or bFGF); tumor necrosis factor alpha (TNF-alpha) and tumor necrosis factor beta (TNF-beta); calcitonin; hematoprotein; plasminogenic activators and their precursors (t-PA, urokinase, pro-urokinase, streptokinase, protein C); cytokines; family of TNF ligands (TRAIL, FasL, osteoprotegerin); soluble receptors (p55, p75), growth hormone e.g. human growth hormone, bovine growth hormone and parathyroid hormone; lipoproteins; alpha-1-antitrypsin; insulin, proinsulin, subunit A of insulin, subunit B of insulin; glucagons; blood clotting factors, such as e.g. Factor VIII, Factor IX, tissue factor, von Willebrand factor; bombasine; thrombin; enkephalinase; macrophage inflammatory protein (MIP-1-alpha); relaxin A subunit, relaxin B subunit, prorelaxin; inhibin; activin; vascular endothelial growth factor (VEGF); hormone receptors or growth factor receptors; integrins; protein A, protein D; rheumatoid factors; bone-derived neurotrophic factor (BDNF), neurotropin-3, -4, -5, or -6; nerve growth factor (NGF); platelet-derived growth factor (PDGF); fibroblast growth factor (aFGF and bFGF); transforming growth factor (TGF-alpha and TGF-beta); insulin-like growth factor (IGF1 and IGF2); thrombopoietin (TPO); bone morphogenetic protein (BMP); superoxide dismutase; biologically active fragments of the above mentioned proteins, and other therapeutically effective proteins.

Therapeutically effective proteins of the present invention are used in therapeutically effective amounts.

The term >>therapeutically effective amount of a protein<< as used herein, refers to the amount of a protein having a therapeutic effect.

The most preferred active pharmaceutical ingredient is G-CSF preferably used in therapeutically effective amounts.

In the context of the present invention the pharmaceutical composition is provided which comprises G-CSF and a non-detergent sulfobetaine (NDSB).

The term >>G-CSF<< as used herein refers to the protein which regulates differentiation and proliferation of hematopoietic cells in mammals and activation of mature cells of the hematopoietic system. It is selected from the group consisting of: human G-CSF and its derivatives and analogues defined below. Preferably, G-CSF relates to the recombinant human G-CSF, produced by the expression in the *E. coli* bacterium.

The pharmaceutical composition of the present invention can be used for all types of G-CSFs; it can be used among others also in the case of isolation of derivatised forms of G-CSF, such as: methionyl G-CSF (Met-G-CSF), glycolised, enzyme- and chemically-modified (such as e.g.: pegylated) G-CSF, G-CSF analogues and fusion proteins which comprise G-CSF.

The term >>therapeutically effective amount of G-CSF<< as used herein, refers to the amount of G-CSF which enables the therapeutic effect of G-CSF.

The pharmaceutical composition of the present invention optionally further comprises a polyol.

The term >>polyol<< refers to any polyhydric alcohol, i.e. a chemical compound containing one or more hydroxyl groups per molecule.

Preferably, the polyol is selected from the group consisting of sorbitol, glycerol, inositol, trehalose, and mannitol. The preferred polyol concentration is in the range from 1% to 10% (m/v).

The pharmaceutical composition of the present invention optionally further comprises one or more of pharmaceutically acceptable excipients.

The pharmaceutically acceptable excipient is selected from the group consisting of metal cation scavengers (e.g. EDTA and similar chelators), solvents and free radical scavengers (e.g. DMSO), various acids (e.g. acetic acid, citronic, methanesulphonic, phosphoric, hydrochloric and other), various bases (e.g. NaOH or organic N bases, e.g. Good's buffers, such as TRIS, TES, HEPES), various buffer systems (e.g. acetic acid/acetate, glutaminic acid/glutamate, maleic acid/maleate, citric acid/citrate, phosphoric acid/phosphate, and others), various pharmaceutically acceptable excipients for the maintenance of isotonicity of the solution (e.g. inorganic salts, such as $CaCl_2$ and NaCl), protein stabilisers, selected from the group consisting of surface active substances, such as: glycol and glycerol esters, macrogol esters and ethers, sorbitan derivatives or polysorbates (polysorbate 20, polysorbate 80), amino acids, poloxamers (Pluronic F68), polyvinylpyrrolidone (PVP), and other. Preferably, the pharmaceutically acceptable excipient is selected from the group consisting of EDTA and DMSO.

The NDSB in the pharmaceutical compositions of the present invention can be combined with one or more of the above mentioned pharmaceutically acceptable excipients.

The term >>stabilizer<< as used herein, refers to a pharmaceutically acceptable excipient that may stabilize an active pharmaceutical ingredient (e.g. a protein e.g. G-CSF).

The term >>protein stabilizer<< as used herein, refers to a pharmaceutically acceptable excipient that may stabilize a protein (e.g. G-CSF).

The term >>protein stability<< (e.g. G-CSF) as used herein refers to the maintenance of protein content (e.g. G-CSF), as well as to the maintenance of protein biological activity (e.g. G-CSF). The decrease of protein stability (e.g. of G-CSF) may be influenced, among others, by the following processes: protein adsorption to the container walls, denaturation or degradation of protein, as well as aggregate formation, for e.g. protein dimer (e.g. G-CSF dimer) and/or protein multimer (e.g. G-CSF multimer) and/or similar molecules with higher molecular mass. These processes may be the result of various factors, e.g. increased temperature, inappropriate containers, use of inappropriate protein stabilisers, light exposure, freezing/thawing, inappropriate manufacturing procedure and/or inappropriate storage.

The pharmaceutical composition of the present invention may stabilize the protein (e.g. G-CSF) at temperatures above refrigerator temperature (2-8° C.), and also at room temperature (i.e. below 25° C.) and even higher temperatures (e.g. about 40° C.).

The pharmaceutical composition of the present invention may comprise only one pharmaceutically acceptable excipient, i.e. NDSB for protein stabilisation (e.g. G-CSF) and for maintenance of suitable pH of the solution.

Accordingly, in a further aspect of the present invention a pharmaceutical composition is provided which comprises an active pharmaceutical ingredient (as outlined above) and a NDSB as the sole further excipient.

NDSB in the pharmaceutical composition represents a protective molecule which stabilises protein and therefore stands for protein stabilisers which are used in other pharmaceutical compositions (e.g. sugars, amino acids and other), as well as a molecule which adjusts a suitable pH of the solution and in this way is used instead of acids (e.g. acetic, citric, methanesulphonic, phosphoric, hydrochloric acid and others), which are used for the adjustment of suitable pH of the solution in other pharmaceutical compositions. NDSBs can also maintain a suitable pH and therefore replace various buffer systems and/or their combinations used in other pharmaceutical compositions (e.g. acetic acid/acetate, glutaminic acid/glutamate, maleic acid/maleate, citric acid/citrate, phosphoric acid/phosphate, and other). In comparison to the use of two or more molecules with different functions, the use of one molecule with several different functions is better with regard to the economy of preparation, lower costs, as well as easier and quicker preparation of the pharmaceutical composition, and also for the patient himself, as concerns the intake of less additional substances into the body. The characteristics of NDSB present an additional advantage, for it is a simple molecule which is not sensitive to light, temperature, various oxidizing agents (e.g. air oxygen), hydrolysis, is not chemically reactive molecule, has the zwitterion nature in wide pH area, which means that the mechanism of interaction in wide pH range does not change substantially.

An aspect of the present invention is use of a NDSB as a stabilizer in a pharmaceutical composition.

An aspect of the present invention is use of a NDSB as a protein stabilizer in a pharmaceutical composition.

An aspect of the present invention is use of a NDSB as a pH adjustment agent in a pharmaceutical composition.

An aspect of the present invention is use of a NDSB as a buffering agent in a pharmaceutical composition.

The preferred pharmaceutical composition of the present invention is a liquid pharmaceutical composition; this does not however, limit usage of NDSBs in lyophilised pharmaceutical protein-comprising compositions in the context of the present invention.

The pharmaceutical composition of the present invention enables parenteral administration subcutaneously, intravenously or intramuscularly without reconstitution, dilution or additional prior preparation which could lead to a decrease of the activity of the active pharmaceutical ingredient, e.g. protein e.g. G-CSF and to additional technical problems at the time of administration.

Preferably, the pharmaceutical composition of the present invention does not contain human serum proteins with which viral contamination is possible. In this way the probability of occurrence of various allergic reactions, which could be the result of administration of human serum albumins, is reduced. It is prepared in isotonic solution which is pharmaceutically acceptable and does not cause undesirable effects.

In the pharmaceutical composition of the present invention, therapeutically effective amount of a protein corresponds to therapeutically effective amounts of protein that are present on the market. In the case of use of G-CSF, therapeutically effective amount of G-CSF is selected from the range between 0.3 mg/ml and 1.2 mg/ml, which does not, however, limit the present invention.

The pharmaceutical composition of the present invention can be used for preparation of medicaments (for treatment) and for treatment of diseases indicated for therapeutically effective proteins, enumerated above.

The pharmaceutical composition of the present invention can also be used for the treatment of all diseases and for preparation of medicaments for treatment of all diseases for which G-CSF is indicated. The indicated diseases may be selected from the group consisting of: neutropenia and its clinical sequelae, reduced hospitalisation in febrile neutropenia after chemotherapy, mobilisation of hematopoietic germ cells, alternative infusion of donor leukocytes, chronic neutropenia, neutropenic and non-neutropenic infections, transplantation receivers, chronic inflammatory diseases, sepsis and septic shock, reduced risk, reduced morbidity, reduced mortality and reduced number of hospitalisation days in neutropenic and non-neutropenic infections, prevention of infections and complications of infections in neutropenic and non-neutropenic patients, prevention of nosocomial infections and reduced mortality and frequence of nosocomial infections, enteral application to newborn babies, enforcement of the neonate immune system, improvement of the clinical result in patients at intensive care unit and in critically ill patients, vaccination and management of burns, skin ulcers and lesions, intensification of chemotherapy and/or radiotherapy, pancytopenia, increase in anti-inflammatory cytokines, reduction of high dosage chemotherapy intervals with prophylactic use of G-CSF, potentiation of anti-tumor effects of photodynamic therapy, prevention and management of diseases caused by various cerebral dysfunctions, treatment of thrombotic diseases and their complications and post-radiation recovery of erythropoiesis.

An aspect of the present invention is use of a NDSB for the preparation of a pharmaceutical composition.

The pharmaceutical composition of the present invention can be filled in pharmaceutical packaging selected from the group consisting of ampoules, injection syringes and vials. This pharmaceutical packaging enables the application in volumes in the range from 0.2 ml to 2 ml (per dose).

Furthermore, the object of the invention is also the process for preparation of the pharmaceutical composition of the present invention. The process for preparation of the pharmaceutical composition of the present invention comprises mixing of a NDSB with therapeutically effective amount of an active pharmaceutical ingredient (e.g. of protein, e.g. G-CSF)

The present invention is illustrated in detail by the following examples but is not restricted thereto. In particular, the examples relate to preferred embodiments of the present invention.

EXAMPLES

Analytical Methods

The following methods are used for the analysis of the pharmaceutical composition of the present invention: high-performance liquid chromatography with size exclusion (SE-HPLC), reversed phase HPLC (RP-HPLC), sodium dodecyl-sulfate polyacrylamide gel electrophoresis (SDS-PAGE), and measurement of the in vitro biological activity.

SE-HPLC

SE-HPLC is used to determine concentrations of G-CSF aggregates, particularly of dimers and higher aggregates. The limit of detection for determination of dimers and higher aggregates is 0.01%.

High performance liquid chromatography (HPLC) consists of: UV detector, online degasser, binary pump module and thermostated autosampler (e.g. Waters Alliance HPLC systems). The analysis is performed under the following conditions:

Chromatographic conditions:
Column: TSK G3000 SW, 10 µm, 300×7.5 mm ID
Column temperature: 30° C.
Mobile phase: phosphate buffer pH 7.0 (5 mM sodium phosphate, 50 mM NaCl)
Flow rate: 0.8 ml/min, isocratic manner
Detection: UV-detector, wavelength 215 nm.
Injection volume: 20 µl (amount of the injected protein: 6-12 µg)
Autosampler temperature: +2 to +8° C.
Run time: 20 minutes.

RP-HPLC

RP-HPLC is used to determine G-CSF content and for quantitative determination of impurities which vary according to the degree of hydrophobicity.

The HPLC system consists of: a UV detector, online degasser, a binary pump module and thermostated autosampler and thermostated column department (e.g. Waters Alliance HPLC systems). The analysis is performed under the following conditions:

Chromatographic conditions:
Column: YMC-Pack ODS-AQ, 200 Å, spherical, 3 µm, 150× 4.6 mm i.d.
Column temperature: 65° C.
Mobile phase: Phase A: 0.1% trifluoro-acetic acid (TFA) and 50% acetonitrile (ACN) in water
Phase B: 0.1% TFA and 95% ACN in water for HPLC
Flow rate: 1.0 mL/min, gradient:

| Time [min] | Mobile phase B [%] |
|---|---|
| 0.0 | 8 |
| 4.0 | 8 |
| 19.0 | 28 |
| 19.1 | 100 |
| 21.0 | 100 |
| 21.1 | 8 |
| 25.0 | 8 |

Detection: UV-detector, wavelength 215 nm.
Injection volume: 10 µL (injected amount of protein: 3-6 µg)
Autosampler temperature: +2 to +8° C.
Run time: 25 minutes.

SDS-PAGE

The SDS-PAGE is used for visual detection of protein dimers present and other aggregated forms (trimers and forms with high molecular mass).

The loading samples are prepared in the loading buffer free of reducing agent. The vertical SDS-PAGE, NuPAGE Bis-Tris 12% gel 8×8 cm, thickness 1.0 mm, 15 lanes (Invitrogen) in MOPS SDS electrophoresis buffer (Invitrogen). Electrophoresis runs 1 hour at constant voltage of 200 V. Samples are coloured with Commassie blue colour (0.1% Phast Gel Blue R 350 in 30% methanol).

Testing In Vitro Biological Activity of G-CSF

Biological activity of G-CSF is determined by the method based on stimulation of cellular proliferation (NFS-60 cells) using the known method (Hammerling, U. et al. in *J Pharm Biomed Anal* 13, 9-20 (1995)) and the use of international standard Human recombinant G-CSF (88/502, yeast cell derived; NIBSC Potters Bar, Hertfordshire, UK; see Mire-Sluis, A. R. et al. v *J Immunol Methods* 179, 117-126 (1995)

Measurement of pH Value pH is measured using MA 5741 (Iskra) pH meter and Biotrode (Hamilton) electrodes. The pH meter is calibrated to the pH range from 3.0 to 5.0 with suitable fresh calibration buffers. The pH is measured at a temperature 25° C. The standard deviation of the pH measurement is 0.003 of the pH value (0.3%).

The Conditions for Testing the G-CSF Stability in Pharmaceutical Compositions

4° C.: stored in refrigerator at the refrigerator temperature (in the range from +4° C. to +6° C.)

40° C.: stored at 40° C.±2° C.

25° C.: stored at room temperature between 25° C. and 30° C. in 1-ml filled syringes during shaking at 75 rpm on the shaker Vibromix 314EVT.

Example 1

Stability Tests

The following liquid pharmaceutical compositions are prepared:

FP1 0.3 mg/ml G-CSF, 39 mM NDSB, 5 mM Na EDTA, pH 4.4
FP2 0.3 mg/ml G-CSF, 39 mM NDSB, 5 mM Na EDTA, 5% DMSO pH 4.4
FP3 0.3 mg/ml G-CSF, 7 mM NDSB, 5% sorbitol, pH 4.4
FP4 0.6 mg/ml G-CSF, 6 mM NDSB, 8% sorbitol, pH 4.6
FP5 0.6 mg/ml G-CSF, 13 mM NDSB, 8% sorbitol, pH 4.3
FP6 0.6 mg/ml G-CSF, 10 mM NDSB, 8% sorbitol, pH 4.5
FP7 0.6 mg/ml G-CSF, 10 mM NDSB, 5% sorbitol, pH 4.4
FP8 0.6 mg/ml G-CSF, 10 mM NDSB, 10% sorbitol, pH 4.4
FP9 0.6 mg/ml G-CSF, 10 mM NDSB, 8% inositol, pH 4.4
FP10 0.6 mg/ml G-CSF, 10 mM NDSB, 8% trehalose, pH 4.4
FP11 0.6 mg/ml G-CSF, 50 mM NDSB, 8% sorbitol, pH 4.9.

Reference pharmaceutical composition:
A (S16-10ACT): 0.3 mg/ml G-CSF, 10 mM acetic acid, 5% (m/v) sorbitol, 0.004% Tween 80, pH adjusted to 4.0 with NaOH (identical to Neupogen).

Samples with a G-CSF concentration of 0.6 mg/ml are stored at 40° C. for 1 month. They are analysed using SE-HPLC; 6 µg of G-CSF is loaded to the column. FIG. 1 shows the respective results (AU=absorption unit).

Legend of FIG. 1:
1 FP1
2 FP2
R S16-10ACT

Samples with concentration G-CSF 0.6 mg/ml are stored at 40° C. for 1 month. Samples are analysed using SE-HPLC; the G-CSF application to the column is 6 µg. The results are shown in FIG. 2 (AU=absorption unit).

Figure 2:
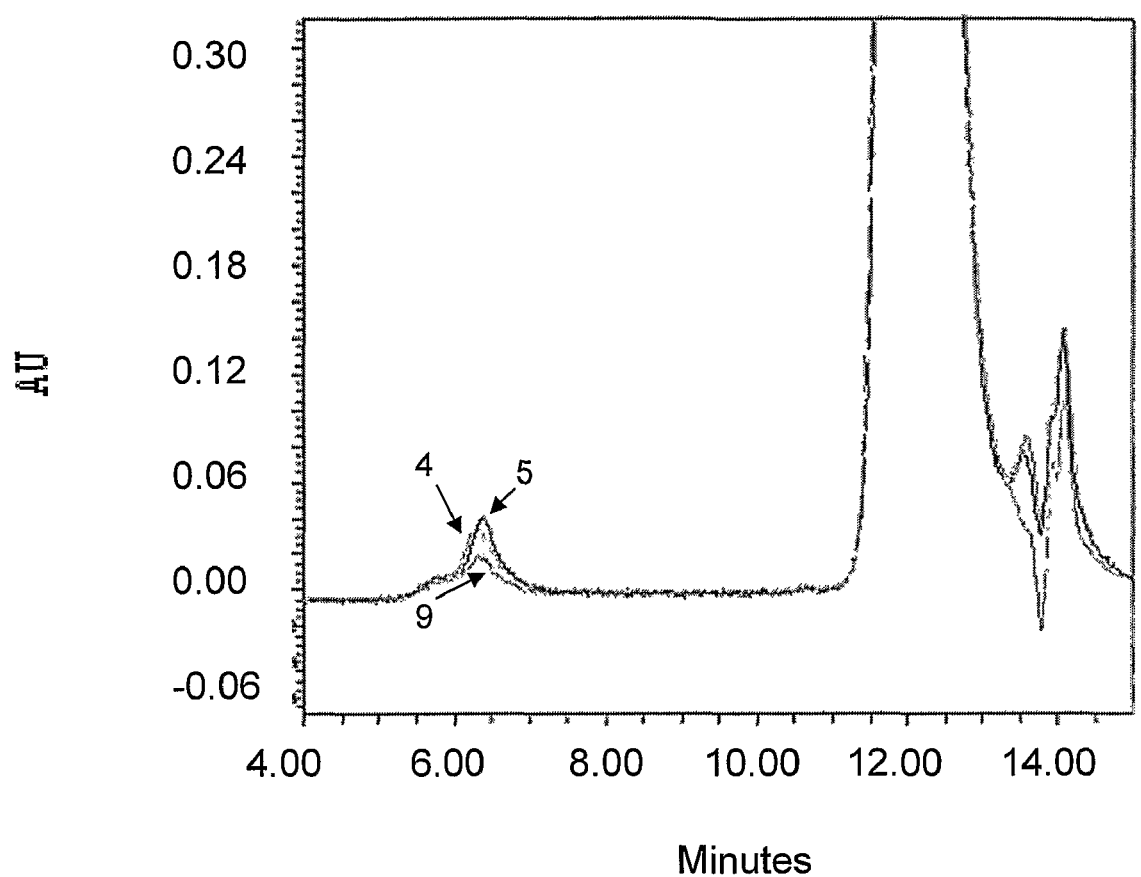
FIG. 2: SE-HPLC of invention samples, stored at 40° C. (±2° C.) for 1 month (40).

Legend of FIG. 2:
4 FP4
5 FP5
9 FP9

Results of Stability Tests

The SE-HPLC analysis of the samples FP1 and FP2, stored for 1 month at 40° C., shows that the samples are stable as there are no visible increase in the content of aggregates and hydrophobic degradation products (Table 1, FIG. 1). The stability is comparable to reference sample (AS16-10ACT) which are identical to the pharmaceutical composition comprising G-CSF, and available on the market (Neupogen, G-CSF=0.3 mg/ml). Stability is also confirmed with RP-HPLC analyses which do not show essential changes in impurities or in the protein content after the storage period. These results comply with the results of the SDS-PAGE analysis (the results are not indicated) and the in vitro measurement of biological activity. The in vitro biological activity of G-CSF, which is used in the studies, is at the level of the international standard (Cat. no. 88/502; NIBSC, UK). The in vitro biological activity of the samples FP1 and FP2 does not change after storage under test conditions (the results are not shown).

TABLE 1

| | NDSB | pH | Excipient | Storage period | Temperature | Dimers (SE-HPLC) | Higher aggregates (SE-HPLC) |
|---|---|---|---|---|---|---|---|
| AS16-10ACT c = 0.3 mg/ml | — | 4.0 | Tween 80 sorbitol | 1 m | 40° C. | 0.00% | 0.13% |
| FP1 | 39 mM | 4.4 | EDTA | 1 m | 40° C. | 0.00% | 0.18% |
| FP2 | 39 mM | 4.4 | EDTA DMSO | 1 m | 40° C. | 0.00% | 0.23% |
| FP3 | 7 mM | 4.4 | sorbitol | 1 m | 40° C. | 0.00% | 1.02% | m: month; %: dimer amount/higher aggregates with reference to the total amount of G-CSF; c = G-CSF concentration.

The results show that the stability of pharmaceutical compositions comprising NDSBs are comparable to the reference sample (AS16-10ACT). Higher NDSB concentrations reveal a more favourable effect on the stability.

The SE-HPLC analysis of the samples from FP4 to FP11, stored at 25° C. for 1 week and 1 month, shows that the samples are stable as there are no noticeable increase in the aggregate content and in hydrophobic degradation products (Table 2, FIG. 2). Stability is comparable to that of the reference sample (AS16-10ACT), which is identical to G-CSF comprising pharmaceutical composition and which is present on the market (Neupogen, G-CSF=0.3 mg/ml). Stability is also confirmed with the RP-HPLC analyses which do not show essential changes in the impurities or protein content after the storage period. These results comply with the results of the SDS-PAGE analysis (the results are not indicated) and measurement of the in vitro biological activity. The in vitro biological activity of G-CSF, which is used in the studies, is at the level of the international standard (Cat. no. 88/502; NIBSC, UK). After storage under the study conditions, the in vitro biological activity of the samples from FP4 to FP11 is changed (the results are not shown).

TABLE 2

| Sample | pH | Excipient | Storage period | Temperature | Dimers (SE-HPLC) | Higher aggregates (SE-HPLC) | Protein content (RP-HPLC) |
|---|---|---|---|---|---|---|---|
| FP4 | 4.6 | sorbitol 8% | 1 w | 40° C. | 0.07% | 0.21% | 99.4% |
| 6 mM | | | 1 m | 40° C. | 0.00% | 1.8% | 95.3% |
| NDSBs | | | 1 w shaking | 25° C. | 0.03% | 0.07% | 99.6% |

TABLE 2-continued

| Sample | pH | Excipient | Storage period | Temperature | Dimers (SE-HPLC) | Higher aggregates (SE-HPLC) | Protein content (RP-HPLC) |
|---|---|---|---|---|---|---|---|
| FP5 | 4.3 | sorbitol 8% | 1 w | 40° C. | 0.10% | 0.18% | 96.5% |
| 13 mM | | | 1 m | 40° C. | 0.00% | 1.63% | 93.9% |
| NDSBs | | | 1 w shaking | 25° C. | 0.00% | 0.07% | 97.4% |
| FP6 | 4.5 | sorbitol 8% | 1 w | 40° C. | 0.13% | 0.18% | 98.8% |
| 6 mM | | | 1 m | 40° C. | 0.00% | 1.82% | 96.0% |
| NDSBs | | | 1 w shaking | 25° C. | 0.05% | 0.07% | 99.2% |
| FP7 | 4.4 | sorbitol 5% | 1 w | 40° C. | 0.18% | 0.17% | 98.6% |
| 10 mM | | | 1 m | 40° C. | 0.00% | 1.18% | 95.1% |
| NDSBs | | | 1 w shaking | 25° C. | 0.02% | 0.04% | 99.4% |
| FP8 | 4.4 | sorbitol 10% | 1 w | 40° C. | 0.11% | 0.18% | 98.4% |
| 10 mM | | | 1 m | 40° C. | 0.00% | 1.9% | 95.8% |
| NDSBs | | | 1 w shaking | 25° C. | 0.03% | 0.08% | 99.6% |
| FP9 | 4.4 | inositol 8% | 1 w | 40° C. | 0.10% | 0.09% | 98.4% |
| 10 mM | | | 1 m | 40° C. | 0.00% | 0.97% | 95.6% |
| NDSBs | | | 1 w shaking | 25° C. | 0.16% | 0.08% | 99.4% |
| FP10 | 4.4 | trehalose 8% | 1 w | 40° C. | 0.35% | 0.25% | 98.4% |
| 10 mM | | | 1 m | 40° C. | 0.00% | 2.08% | 95.2% |
| NDSBs | | | 1 w shaking | 25° C. | 0.50% | 0.11% | 99.0% |
| FP11 | 4.9, | sorbitol 8% | 1 w | 40° C. | 0.16% | 0.05% | 97.0% |
| 50 mM | pH | | 1 m | 40° C. | 0.14% | 0.85% | 89.1% |
| NDSBs | with NaOH | | 1 w shaking | 25° C. | 0.05% | 0.05% | 99.1% | w: week, m: month; %: amount of dimer/higher aggregates with reference to the total amount of G-CSF; % polyol: m/v.

The results from Table 2 show that pharmaceutical compositions with the addition of NDSBs are stable. A slight reduction of stability with regard to the reference sample (Table 1) is noted in samples which are exposed to more extreme conditions (1 month, 40° C.). It is also possible that a slight reduction of stability results from the fact that pH above 4.0 is not favourable for G-CSF, which is also evident from the state of the art. The reference sample is prepared using pH 4.0.

Example 2

Composition of Inventive Pharmaceutical Compositions of G-CSF

The compositions of inventive pharmaceutical compositions are presented in Table 3.

TABLE 3

| Sample | G-CSF content (mg/ml) | Inactive ingredients | pH |
|---|---|---|---|
| FP1 | 0.3 | 39 mM NDSB, 5 mM Na EDTA, 5% DMSO | 4.4 |
| FP2 | 0.3 | 39 mM NDSB, 5 mM Na EDTA | 4.4 |
| FP3 | 0.3 | 7 mM NDSB, 8% sorbitol | 4.4 |
| FP4 | 0.6 | 6 mM NDSB, 8% sorbitol | 4.6 |
| FP5 | 0.6 | 13 mM NDSB, 8% sorbitol | 4.3 |
| FP6 | 0.6 | 10 mM NDSB, 8% sorbitol | 4.5 |
| FP7 | 0.6 | 10 mM NDSB, 5% sorbitol | 4.4 |
| FP8 | 0.6 | 10 mM NDSB, 10% sorbitol | 4.4 |
| FP9 | 0.6 | 10 mM NDSB, 8% inositol | 4.4 |
| FP10 | 0.6 | 10 mM NDSB, 8% trehalose | 4.4 |

Bulk Concentrate Preparation

The starting material of G-CSF for the preparation of bulk concentrate is produced by the expression in *E. coli*.

Bulk concentrate is prepared in solution with pure acid (acetic acid or HCl) at pH 4.4 using the G-CSF concentration 1.5 mg/ml. The SE-HPLC analysis of the bulk concentrate shows that the content of dimers and of higher aggregates is below the detection limit. The assay of impurities, determined with the RP-HPLC analysis, is in the range 2-4%. (The RP-HPLC analysis of a fresh Neupogen sample shows a comparable amount of impurities).

Quality of Substances

NDSB: NDSB-195 (Calbiochem) for analysis, sorbitol: Ph. Eur. quality; glycerol: Merck; for analysis; inositol: myo-inositol (Fluka: >99.5% HPLC), trehalose (Fluka: >99.5% HPLC), EDTA (Sigma: 99%), DMSO (Merck: >99.5%), Tween 80 (Sigma, low peroxide level, contains BHT as an antioxidant); water for injection: Ph. Eur. quality; water for analysis: Milli-Q (Millipore).

Preparation of Reference Pharmaceutical Composition

A (S16-10ACT): The fractions of the gel filtration which comprise the G-CSF monomer are pooled and substituted with buffer containing 10 mM of acetic acid and 5% of sorbitol in water for injection. pH of the buffer is adjusted with NaOH solution to 3.96. The substitution is performed on the Labscale™ TFF System/Millipore, using three Ultracel-5 PLCCC membranes. Tween 80 is added until a concentration of 0.004% is obtained. pH of the final solution after substitution is 4.0, with concentration of 0.304 mg/ml.

Preparation of Inventive Pharmaceutical Compositions:

General:

The inventive pharmaceutical compositions are prepared with dilution of bulk concentrate with an adequate sterile buffer solution, previously filtered through a 0.2 PES/Nalgene filter. The final G-CSF concentration is 0.3 mg/ml or 0.6 mg/ml, respectively.

The pharmaceutical compositions FP1 and FP2 are filled in 2 ml vials made of colourless glass, hydrolytic type 1, washed, sterilised and closed with closures from brombutyl rubber, equipped with aluminium caps.

Other pharmaceutical compositions (FP3 to FP11) are (manually) filled in the injection syringes (volume 1.3-1.4 ml) so that there is minimal amount of air around the closure.

FP1, FP2, FP3: To 1 portion of the bulk concentrate 4 portions of the suitable buffer solution are added. Final concentrations indicated in Table 3 are obtained. pH is no longer adjusted.

FP4-FP11: To 4 portions of the concentrate 6 portions of the solution with an suitable buffer are added. Final concentrations indicated in Table 3 are obtained. pH is no longer adjusted.

The invention claimed is:

1. A pharmaceutical composition for parenteral administration which comprises an active pharmaceutical ingredient and from 1 to 1000 mM of a non-detergent sulfobetaine (NDSB)
    wherein the NDSB is a quaternary ammonium salt having a nitrogen atom and four groups R1, R2, R3, and R4-SO$^-_3$ bound to the nitrogen atom, wherein R1, R2 and R3 can be the same and/or different and are selected from the group consisting of one or more of methyl, ethyl, propyl, butyl, pentyl, hexyl and derivatives thereof, and R4 is (CH$_2$)$_n$, wherein n is from 1 to 6, and wherein the pharmaceutical composition is suitable for parenteral administration.

2. The pharmaceutical composition according to claim 1, wherein the active pharmaceutical ingredient is selected from the group consisting of a therapeutically effective synthetic or natural organic molecule and a therapeutically effective protein.

3. The pharmaceutical composition according to claim 2, wherein the therapeutically effective protein is selected from the group consisting of granulocyte-colony stimulating factor, interferons, interleukins, granulocyte-macrophage colony-stimulating factor, macrophage colony-stimulating factor, epidermal growth factor, erythropoietin, follicle-stimulating hormone, human serum albumin, deoxyribonuclease, fibroblast calcitonin, hematoprotein; plasminogenic activators and their precursors, cytokines; TNF family of ligands, soluble receptors, growth hormones, lipoproteins; alpha-1-antitrypsin; insulin, proinsulin, subunit A of insulin, subunit B of insulin; glucagons; blood coagulation factors, bombasine; thrombin; enkephalinase; macrophage inflammatory protein (MIP-1-alpha); relaxin A subunit, relaxin B subunit, prorelaxin; inhibin; activin; vascular endothelial growth factor; hormone receptors or growth factor receptors; integrins; protein A, protein D; rheumatoid factors; bone-derived neurotrophic factor, neurotropin-3, -4, -5, or 6; nerve growth factor, platelet-derived growth factor, fibroblast growth factor, transformed growth factor, insulin-like growth factor, thrombopoietin, bone morphogenetic protein and superoxide dismutase.

4. The pharmaceutical composition according to claim 3, wherein the therapeutically effective protein is G-CSF.

5. The pharmaceutical composition according to claim 1, wherein the NDSB is selected from the group consisting of dimethylethyl-(3-sulphopropyl)-ammonium salt, 3-(1-pyridino)-1-propanesulfonate, dimethylbenzylammonium propanesulfonate, dimethyl-t-butyl-(3-sulphopropyl)ammonium salt, 3-(1-methylpiperidine)-1-propanesulfonate and dimethyl-(2-hydroxyethyl)-(sulphopropyl)-ammonium salt.

6. The pharmaceutical composition according to claim 5, wherein the NDSB is dimethyl-t-butyl-(3-sulphopropyl)ammonium salt.

7. The pharmaceutical composition according to claim 1 wherein said composition optionally further comprises a polyol.

8. The pharmaceutical composition according to claim 7, wherein the polyol is selected from the group consisting of sorbitol, glycerol, inositol, trehalose and mannitol.

9. The pharmaceutical composition according claim 1, wherein said composition optionally further comprises one or more pharmaceutically acceptable excipients.

10. The pharmaceutical composition according to claim 9, wherein a pharmaceutically acceptable excipient is selected from the group consisting of EDTA and DMSO.

11. A process for preparation of a pharmaceutical composition, wherein the pharmaceutical composition of claim 1 is prepared by mixing a NDSB with therapeutically effective amount of an active pharmaceutical ingredient.

* * * * *

UNITED STATES PATENT AND TRADEMARK OFFICE
CERTIFICATE OF CORRECTION

| | | |
|---|---|---|
| PATENT NO. | : 7,906,109 B2 | Page 1 of 1 |
| APPLICATION NO. | : 10/583157 | |
| DATED | : March 15, 2011 | |
| INVENTOR(S) | : Viktor Menart, Gaberc Porekar and Barbara Podobnik | |

It is certified that error appears in the above-identified patent and that said Letters Patent is hereby corrected as shown below:

Column 2, lines 30, 31 and 32, for the Celsius symbol "C." each occurrence should read --C--.

Column 3, line 54, delete "«0" and insert therefore --«--.

Column 5, lines 40, 41 and 42, for the Celsius symbol "C." each occurrence should read --C--.

Column 7, line 50, the Celsius symbol "C." should read --C--.

Column 8, lines 61, 62, 63 and 64, for the Celsius symbol "C." each occurrence should read --C--.

Column 9, lines 40 and 49 for the Celsius symbol "C." each occurrence should read --C--.

Column 10, line 3, the Celsius symbol "C." should read --C--.

Column 10, in Table 1, under the column "Temperature," for the Celsius symbol "C." each occurrence should read --C--.

Column 10, in Table 2, under the column "Temperature," for the Celsius symbol "C." each occurrence should read --C--.

Column 11, in Table 2-continued, under the column "Temperature," for the Celsius symbol "C." each occurrence should read --C--.

Column 11, line 35, the Celsius symbol "C." should read --C--.

Signed and Sealed this
Fourth Day of October, 2011

David J. Kappos
*Director of the United States Patent and Trademark Office*